United States Patent [19]

Doyle

[11] 4,030,504
[45] June 21, 1977

[54] NASAL HEMOSTAT AND METHOD OF CONSTRUCTION OF NASAL HEMOSTAT

[76] Inventor: Donald E. Doyle, 8147 Armor Road, Los Angeles, Calif. 90046

[22] Filed: Aug. 15, 1975

[21] Appl. No.: 605,148

[52] U.S. Cl. .............................. 128/325; 128/342
[51] Int. Cl.² ................. A61B 17/12; A61M 29/02
[58] Field of Search .................. 128/325, 341, 342

[56] References Cited

UNITED STATES PATENTS

| 438,929 | 10/1890 | Knight | 128/341 |
|---|---|---|---|
| 2,179,964 | 11/1939 | Stevens | 128/325 X |
| 3,049,125 | 8/1962 | Kriwkowitsch | 128/325 |
| 3,570,494 | 3/1971 | Gottschalk | 128/325 |
| 3,705,585 | 12/1972 | Saffro | 128/325 X |

*Primary Examiner*—Channing L. Pace

[57] ABSTRACT

A nasal hemostat, adapted for insertion into a nasal cavity, is composed of contracted material adapted to expand into a porous tampon upon contact with a fluid. The contracted tampon is in the form of an elongated cylinder. Upon expansion, the tampon assumes a domed shape, having a linear bottom wall, a convex top wall, and two parallel side walls. A substantially rectangular tongue continuous with the bottom wall protrudes from the posterior end of the expanded tampon. Two elongated recesses are formed longitudinally in one of the side walls. Upon expansion, these recesses receive the inferior and middle conchae of the nasal cavity lateral wall so that the expanded tampon will apply hemostatic pressure to substantially all parts of the nasal cavity. The rearwardly extending tongue, when in operative position, preferably terminates short of the pharyngeal orifice of the auditory tube. An elongated breathing tube extends longitudinally through the contracted tampon from the anterior end to the posterior end. The tube is positioned to extend through the tongue at the posterior end to allow nasal breathing when the tampon is expanded.

9 Claims, 7 Drawing Figures

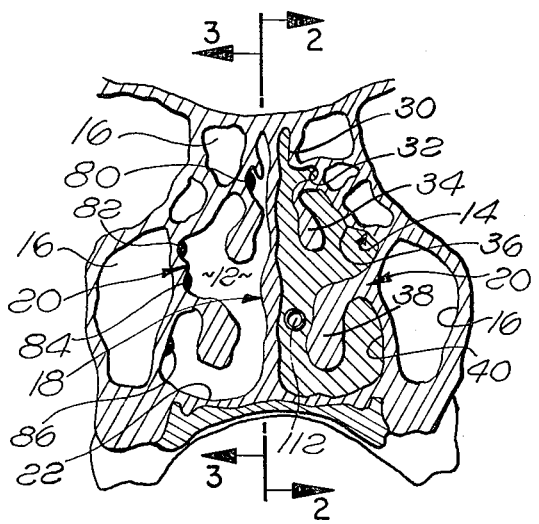
FIG.1.
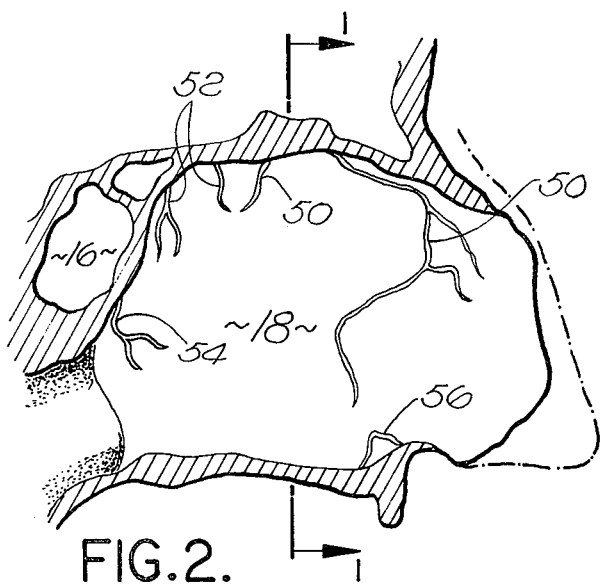
FIG.2.
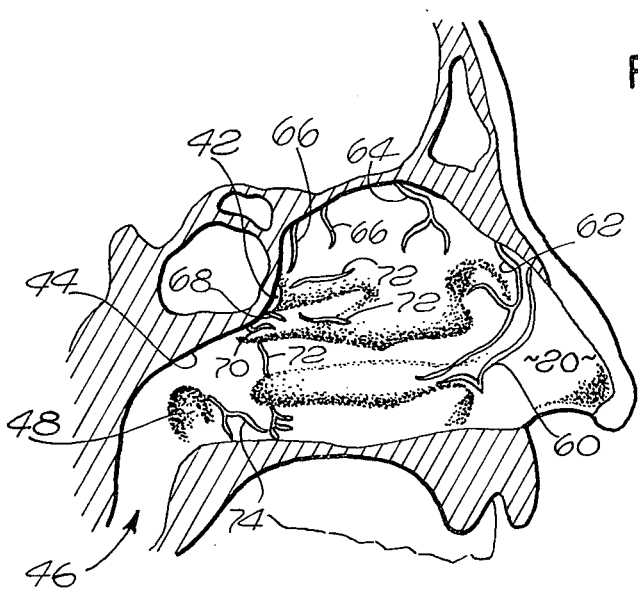
FIG.3.
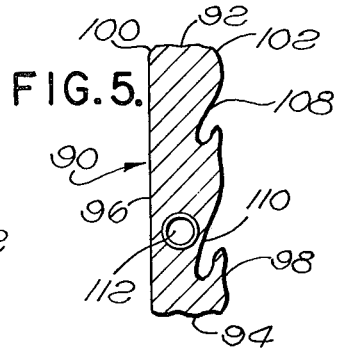
FIG.5.
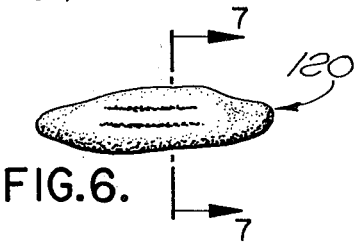
FIG.7.
FIG.6.
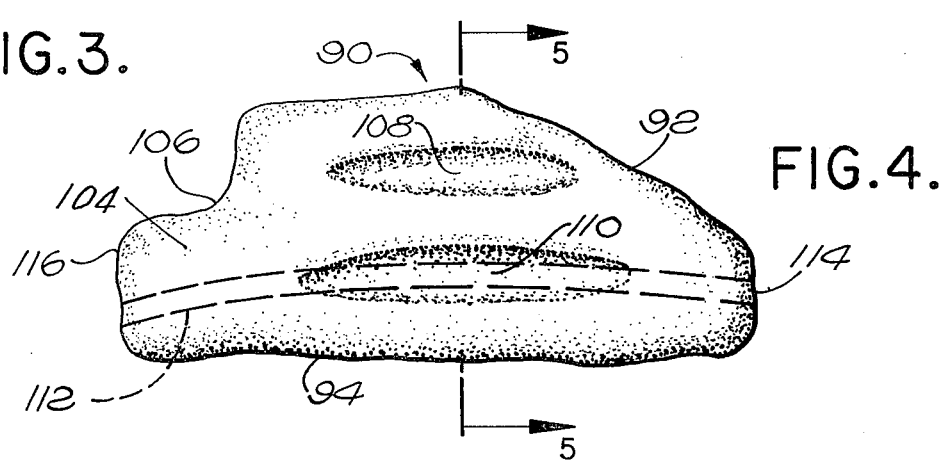
FIG.4.

NASAL HEMOSTAT AND METHOD OF CONSTRUCTION OF NASAL HEMOSTAT

BACKGROUND OF THE INVENTION

This invention relates to hemostats, and particularly to an apparatus for providing hemostatic pressure to substantially all portions of the nasal cavity.

At present, a plurality of guaze cylinders are forced into the nasal cavity, one after another, until sufficient pressure is created to provide a type of nasal hemostat. Such a procedure is extremely awkward, time consuming and painful. In addition, the guaze cylinders frequently fail to apply pressure to the specific blood vessels which have been ruptured. More recently, a type of balloon has been employed to expand in the nasal cavity for the same purpose. While this procedure is less time consuming and painful, it also is often ineffectual in applying hemostatic pressure to the specific blood vessels which have been ruptured.

Even more recently, nasal tampons, formed of a compressed cellulose material which expands upon contact with fluids, have been employed to attempt to solve the problem of applying appropriate hemostatic pressure. These tampons, however, operate in a manner similar to the balloon in frequently failing to apply hemostatic pressure to the ruptured blood vessels.

In addition, all of these prior apparatus and methods block the nasal cavity, thus forcing the patient to breathe through his mouth. This produces dryness of the tongue and throat, and frequently cracking of the lips and tongue. Nasal breathing, on the other hand, is more physiological and less disquieting to the patient. Furthermore, nasal breathing has been found to be much more efficient due to the back pressure created during exhaling through the nose.

I have discovered that the reason for the failure of these prior art methods and apparatus to satisfactorily stop nasal bleeding is their inability to apply hemostatic pressure to substantially all portions of the nasal cavity, including the blood vessels which are hidden in cavities underneath protruding bones. Thus, the invention described and shown herein is contoured to apply hemostatic pressure to all areas of the nasal cavity, including such normally hidden cavities, while at the same time allowing the patient to breathe through his nose.

SUMMARY OF THE INVENTION

A nasal hemostat adapted for insertion into a nasal cavity is composed of a tampon of contracted, expansible material formed to apply pressure against substantially all walls of the nasal cavity when expanded. The expanded tampon thus applies hemostatic pressure to the blood vessels in said walls. A breathing tube extends between the anterior and the posterior ends of the tampon to allow nasal breathing when the tampon is expanded in operative position within the nasal cavity.

In one embodiment of the invention, the expanded tampon has a generally dome-shape with a substantially linear bottom wall, a convex top wall, and two parallel side walls. A substantially rectangular tongue continuous with the bottom wall protrudes from the posterior end of the tampon. One side wall has two longitudinal recesses formed therein to receive the inferior and the middle conchae of the lateral wall of a nasal cavity when the tampon is expanded in operative position. The tongue terminates near the pharynegeal orifice of the auditory tube. The tampon is then contracted and dried so that upon expansion it will apply hemostatic pressure to substantially all parts of the nasal cavity, including the inferior, middle and superior meatus, the inferior, middle and superior conchae, and the sphenoethmoidal recess. The breathing tube extends longitudinally through the tampon and through the tongue to allow nasal breathing when in operative position.

DESCRIPTION OF THE DRAWINGS

The invention may best be understood when the drawings are taken in conjunction with the following detailed description, wherein;

FIG. 1 is a cross-sectional, elevational view taken along a transverse, medial plane of a nose, as indicated by the line 1—1 of FIG. 2, showing the nasal hemostat of one embodiment of this invention inserted in one of the nasal cavities;

FIG. 2 is a cross-sectional, elevational view taken along the line 2—2 of FIG. 1 showing the nasal septum and some of the major arteries carried by the septum;

FIG. 3 is a cross-sectional, elevational view taken along the line 3—3 of FIG. 1 showing the lateral wall of a nasal cavity and some of the major arteries carried by the lateral wall;

FIG. 4 is an elevational view of the nasal hemostat of one embodiment of this invention in expanded form;

FIG. 5 is a cross-sectional, elevational view taken along the line 5—5 of FIG. 4;

FIG. 6 is an elevational view of the nasal hemostat of FIGS. 4 and 5 in contracted form; and, FIG. 7 is a cross-sectional, elevational view taken along the line 7—7 of FIG. 6.

DETAILED DESCRIPTION

A contoured tampon is composed of a compressed porous material adapted to be positioned in a nasal cavity and to expand upon being contracted with a fluid to thus apply hemostatic pressure to substantially all interior parts of the nasal cavity. The tampon, when expanded outside the nasal cavity, is generally dome-shape and has a substantially linear bottom wall 94, a convex top wall 92, two parallel side walls 96 and 98, and a substantially rectangular tongue 104 continuous with the bottom wall and protruding from the posterior end 116 of the tampon. The tongue 104 is formed to terminate short of the pharyngeal orifice 48 of the auditory tube in the majority of cases when in operative position. A side wall 98 of the tampon has two elongated recesses 108 and 110 formed longitudinally in the wall to receive the bone structures or conchae 34 and 38 protruding from the lateral wall of the nasal cavity when the tampon is expanded in operative position. An elongated breathing tube 112 extends longitudinally through the tampon between the anterior and posterior ends to allow nasal breathing when the tampon is expanded in operative position.

More specifically, FIG. 1 is a transverse, cros-sectional, elevational view of a nose structure showing two nasal cavities 12 and 14 and various adjacent sinus cavities 16. Each nasal cavity has two side walls converging at the top of the cavity and a bottom wall 22 forming the floor of the cavity. The interior or medial side walls of the respective nasal cavities are provided by the relatively flat, vertical septum 18 while the outer side walls are provided by the convoluted lateral walls 20. Each lateral wall 20 has three boney ridges or conchae 30, 34 and 38 which extend into the nasal cavity to form three elongated passages or meatus 32, 36 and 40, respectively, extending longitudinally along each lateral wall. Portions of the conchae depend downwardly between adjacent portions of the meatus and the septum. In the embodiment shown in FIG. 1, the concha superior 30 protrudes over the superior meatus 32, the concha media 34 or middle concha depends down over portions of the middle meatus 36, and the concha inferior 38 depends down over portions of the inferior meatus 40.

As is shown in FIGS. 2 and 3, the nasal cavities are generally domed or bowl-shaped in the anterior-posterior plane. In addition, a narrowed or contracted canal 44 at the rear of the nasal cavity provides communication between the nasal cavity and the pharynx 46. At the upper end of the pharynx 46 is positioned the pharyngeal orifice 48 of the auditory tube. The sphenoethmoidal recess 42 is a groove behind and above the superior concha 30.

Due to the complex nature of the recesses, protrusions, and other contours of the nasal cavities, it is difficult to obtain ready access and apply pressure to various blood vessels contained within the nasal cavity. While some of these blood vessels are rather minor, others are of major importance and include relatively large arteries which, because of their proximity to the exposed surfaces of the nasal cavity, are easily ruptured. Various branches of a few of the major arteries which lie on the septum 18, shown in FIG. 2, are the anterior ethmoidal artery 50, the posterior ethmoidal artery 52, the posterior septal branch 54 of the sphenopalantine artery, and the septal branch 56 of the superior labial artery. Various branches of some of the major arteries on the lateral wall 20, shown in FIG. 3, are the lateral nasal branches 60 of the facial artery, the lateral nasal branches 62 of the anterior ethmoidal artery, the anterior ethmoidal artery 64, the lateral nasal branches 66 of the posterior ethmoidal artery, the posterior septal artery 68, the sphenopalantine artery 70, the posterior lateral nasal artery 72, and the ascending palantine branch 74 of the facial artery. Portions of these arteries lie in regions of the nasal cavity which are difficult to reach. For example, FIG. 1 shows a lateral branch 80 of the anterior ethmoidal artery in the superior meatus 32, a branch 82 of the anterior ethmoidal and a branch 84 of the posterior lateral nasal artery in the middle meatus 36, and an ascending palantine branch 86 of the facial artery within the inferior meatus 40.

The nasal hemostat of one embodiment of this invention is shown in the form of an expanded tampon 90 in FIGS. 4 and 5. In this embodiment of the invention, the tampon is composed of a hydrocellulose material which expands in all directions upon contact with a fluid, such as mucus or a saline or water solution. In order to form such a tampon a unit of expanded and dry hydrocellulose is cut, by stamping or the like. The exact dimensions of the contracted tampon may vary depending upon the size of the individual nasal cavity. However, most tampons will be of substantially the same shape having a domed or bowl-shaped top wall 92, a substantially flat bottom wall 94, and two substantially parallel side walls 96 and 98. The top and bottom walls are relatively narrow and the longitudinal edges 100 and 102 where the top and side walls meet are shaved in accordance with the narrow dimensions of the top of the nasal cavity. A substantially rectangular tongue 104 protrudes from the rear of the tampon and is adapted to fit in the canal 44 of the nasal cavity but to terminate either short of or near the pharyngeal orifice 48 of the auditory tube. The concave recess 106 formed by the junction of the top wall 92 and the tongue 104 is contoured to apply pressure to the spheno-palantine artery 70 and other blood vessels at the top inner end of the canal 44. This recess 106 also aids in preventing aspiration of the tampon. Undercut elongated notches 108 and 110 are formed longitudinally along the side wall 98 adapted to contact the lateral wall 20 of one nasal cavity. These notches 108 and 110 receive the middle and inferior conchae 34 and 38 respectively when the tampon is expanded in operative position in a nasal cavity, thereby permitting adjacent portions of the tampon to expand into the middle and inferior meatus 36 and 40, respectively, as is shown in FIG. 1.

A breathing tube 112, composed of a circular cylindrical hollow plastic tube or the like, is positioned in the tampon to extend between the anterior end 114 and the posterior end 116 of the tampon to allow nasal breathing when the tampon is expanded in the nasal cavity. The breathing tube 112 preferably extends through the tampon, between the notch 110 and the side wall 96, and through the tongue 104. In one embodiment of the invention, a hole is formed in the tampon, by boring or the like, to receive the tube 112 which is pushed into the hole.

In the embodiment of the invention shown in FIGS. 4 and 5, which is proportioned for an adult nasal cavity, the distance between the anterior and posterior ends 114 and 116 of the expanded, dry tampon after forming is about 75 millimeters, the distance between the top wall 92 and the bottom wall 94 is about 30 millimeters, and the thickness is about 12 millimeters. The tongue 104 is about 15 millimeters long. The notches 108 and 110 are hook shaped or undercut. The notch 108 has a height of about 7 millimeters and a depth of about 4 millimeters. The notch 110 has a height of about 7 millimeters and a depth of about 5 millimeters. The plastic tube 112 has a substantially circular cylindrical configuration, preferably having a diameter of about 4 millimeters.

After the tampon 90 is formed as is shown in FIGS. 4 and 5, it is wetted with a fluid, such as sterile water, and compressed into a contracted state by centripetally applied forces directed substantially radially inwardly towards the breathing tube 112. Sufficient force is applied to the anterior and posterior ends 114 and 116 to prevent the hydrocellulose from being distended at the ends. The tampon is then dried while under compression so that, upon release of the compressive forces, a contracted tampon 120 is produced having a generally cylindrical fusiform configuration as is shown in FIGS. 6 and 7. Such contracted tampon is easily inserted by persons other than physicians, and is thus suitable for first aid applications.

When the contracted tampon 120 is inserted into a nasal cavity and contacted by fluids, it will expand in all directions, as is shown in FIG. 1, to fill the nasal cavity and provide hemostatic pressure to substantially all of the surfaces of the nasal cavity, including those surfaces otherwise hard to reach such as in the middle meatus 36 and the inferior meatus 40. In addition, the inserted and expanded nasal hemostat 122 is composed of a material which is porous upon expansion, thus allowing the free flow of fluids, such as tears, sinus fluids, and the like, from the nasal cavity.

Since the formed tampon is centripetally contracted instead of folded, the chances of the parts of the tampon becoming lodged in the convolutions of the nasal cavity before full expansion are reduced. In addition, presence of the breathing tube 112 in the tampon aids in developing radial forces which expand the tampon into all of the passages of the nasal cavity so that hemostatic pressure is uniformly applied.

It will be understood that various modifications may be made in the embodiment of the nasal hemostat shown and described herein, all within the scope of the invention. For example, various other materials may be employed and the contours of the nasal hemostat may be altered as required by the characteristics of the particular nasal cavity involved.

What is claimed is:

1. A nasal hemostat adapted for insertion into a nasal cavity, comprising:

a tampon of contracted material adapted to be expanded upon the contact with a fluid, said tampon prior to contraction initially having a generally domed-shape with a substantially linear bottom wall, a convex top wall, two parallel side walls, and a substantially rectangular tongue continuous with said bottom wall protruding from the posterior end of said tampon, a first side wall having an upper and lower elongated recess formed longitudinally therein to respectively receive the middle and inferior conchae of the lateral wall of the nasal cavity when the tampon is operatively positioned, said tongue terminating near the pharynegal orifice of the auditory tube when the tampon is operatively positioned, said contracted tampon being adapted to apply hemostatic pressure to substantially all parts of the nasal cavity when expanded in operative position including the inferior, middle and superior meatus, the inferior, middle and superior conchae, and the sphenoethmoidal recess; and an elongated breathing tube extending longitudinally through said contracted tampon between the anterior and the posterior ends, said tube extending through said tongue to allow nasal breathing when the tampon is expanded in operative position within the nasal cavity.

2. A nasal hemostat as defined in claim 1, wherein a concave recess is formed in the expanded tampon prior to contraction at the junction of said upper wall and tongue, the portions of said tampon forming said concave recess being adapted to apply hemostatic pressure to portions of the sphenopalantine artery when the tampon is expanded in operative position in a nasal cavity.

3. A nasal hemostat as defined in claim 2, wherein said upper and lower elongated recesses are undercut.

4. A nasal hemostat as defined in claim 1, wherein said breathing tube extends through the tampon adjacent the lower recess.

5. A nasal hemostat as defined in claim 1, wherein said top wall is narrower than said bottom wall.

6. A nasal hemostat as defined in claim 1, wherein said breathing tube is a circular cylindrical tube composed of a flexible material.

7. A nasal hemostat as defined in claime 1, wherein said material is hydrocellulose.

8. A nasal hemostat as defined in claim 2, wherein said tampon when expanded in a nasal cavity is adapted to apply hemostatic pressure to portions of the anterior ethmoidal artery, the posterior ethmoidal artery, the posterior septal branch of the sphenopalantine artery, the septal branch of the superior labial artery; lateral nasal branches of the facial artery, lateral nasal branches of the anterior ethomoidal artery, the anterior ethmoidal artery, lateral nasal branches of the posterior ethmoidal artery, the posterior septal artery, the sphenopalantine artery, the posterior lateral nasal artery, and the ascending palantine branch of the facial artery within the nasal cavity.

9. A method of constructing a nasal hemostat from a material which is expansible upon contact with fluids to form a tampon adapted to apply pressure against substantially all of the walls of a nasal cavity when expanded in operative position, comprising the steps of:

forming said tampon with a substantially linear bottom wall, a convex top wall, two substantially parallel side walls, and a substantially rectangular tongue continuous with the bottom wall and protruding from the posterior end of said tampon, said top and bottom walls being relatively narrow;

forming at least an upper and a lower elongated recess longitudinally in a first one of said side walls, said recesses being adapted to respectively receive the middle and inferior conchae of the lateral wall of the nasal cavity when the tampon is expanded in operative position;

positioning an elongated hollow breathing tube within said formed tampon, said tube extending through the tampon from the anterior end through said tongue to allow nasal breathing when the tampon is expanded in operative position;

wetting the formed tampon with a fluid;

compressing the wetted tampon into a contracted state by centripetal forces directed substantially towards the breathing tube so that no portion of said tampon is folded over any other portion of the tampon; and, allowing the compressed tampon to dry in said contracted state.

* * * * *

UNITED STATES PATENT AND TRADEMARK OFFICE
CERTIFICATE OF CORRECTION

PATENT NO. : 4,030,504
DATED : June 21, 1977
INVENTOR(S) : Donald E. Doyle

It is certified that error appears in the above-identified patent and that said Letters Patent are hereby corrected as shown below:

Column 2, Line 38, "contracted" should be --contacted--.

Column 5, Line 31, "pharynegal" should be --pharynegeal--.

Column 6, Line 9, "claime" should be --claim--.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks